United States Patent [19]

Brethour

[11] Patent Number: 5,398,290
[45] Date of Patent: Mar. 14, 1995

[54] SYSTEM FOR MEASUREMENT OF INTRAMUSCULAR FAT IN CATTLE

[75] Inventor: John R. Brethour, Hays, Kans.

[73] Assignee: Kansas State University Research Foundation, Manhatton, Kans.

[21] Appl. No.: 58,005

[22] Filed: May 3, 1993

[51] Int. Cl.⁶ .............................................. G06K 9/00
[52] U.S. Cl. .................................. 382/6; 128/660.01; 364/413.25
[58] Field of Search .................. 386/6, 1, 54; 358/112; 369/412.25; 128/660.01, 660.07; 348/163

[56] References Cited

U.S. PATENT DOCUMENTS 5,060,515 10/1991 Kanda et al. ............................. 382/6
5,224,175 6/1993 Gouge et al. ............................ 382/6

OTHER PUBLICATIONS

J. Clin. Ultrasound 13:87-99, Feb. 1985; Diagnostic Accuracy of Computerized B-Scan Texture Analysis and Conventional Ultrasonography in Diffuse Parenchymal and Malignant Liver Disease.
J. Anim. Science 67:120(Suppl. 1) 1989; #290.
Relationship of Ultrasound Speckle to Marbling Score in Cattle; Kansas State University; by J. R. Brethour; Dec. 14, 1989.
J. Anim. Science 61-122 (Supp 1) 1989; #293.
J. Anim. Science 68(Supp 1) 240; 1990; #35.

Primary Examiner—Joseph Mancuso
Attorney, Agent, or Firm—Hovey, Williams, Timmons & Collins

[57] ABSTRACT

A system for measuring intramuscular fat in live cattle uses an ultrasound device to produce ultrasound image of an interior muscle portion. The image contains speckle caused by the scattering of ultrasound waves by the intramuscular fat. Image data representative of the speckle are analyzed in terms of pixel grey areas in the computer to produce measures of intramuscular fat including partial autocorrelation, correlation in a co-occurrence matrix and nonspeckle area.

11 Claims, 3 Drawing Sheets

SYSTEM FOR MEASUREMENT OF INTRAMUSCULAR FAT IN CATTLE

BACKGROUND OF THE INVENTION

1. Field of the Invention

The present invention concerns the measurement of intramuscular fat, i.e., marbling, in cattle using ultrasound to produce an image of an interior portion of a muscle and then to analyze data representative of that image to produce a measurement of marbling.

2. Description of the Prior Art

The grading systems for beef carcasses emphasize leanness in terms of yield grades and palatability in terms of quality grades, i.e., intramuscular fat or marbling. Marbling is considered an indicator of favorable ogano-leptic properties such as juiciness, flavor and tenderness. The yield and quality grades of beef are determined after slaughter. If these grades could be determined accurately in live cattle, producers would have the ability to cluster live cattle during the feedlot phases on the basis of anticipated grades to satisfy packer and consumer specifications. Additionally, this would enable cattle breeders to select breeding stock on the basis of the desirable grading traits.

Ultrasound techniques have been used with some success for determining anticipated yield grades in cattle. A smooth tissue boundary such as that between subcutaneous fat and muscle results in a specular reflection of the ultrasound that produces a congruent image on the ultrasound monitor. Because of this, ultrasound produces a fairly accurate image of backfat and other attributes predictive of yield grade.

The ultrasound techniques have not been successful, however, in producing images representative of marbling. This is because the intramuscular fat deposits of varying sizes and shapes present discontinuities that cause sound waves to scatter rather than echo back to the ultrasound probe. This scattering causes constructive and destructive interference at the probe in a manner analogous to acoustical noise and produces a graininess or mottling in the ultrasound images known as "speckle." Additionally, as marbling increases, the degree of scatter increases.

In the prior art, various attempts have been made to use the speckle itself as an indicator of marbling. For example, in one prior art technique, the speckle in ultrasound images is analyzed visually. With sufficient experience and training, this technique has provided encouraging results, but requires subjective judgment by an individual; subjective judgment in the grading of beef has been a problem in the prior art because it leads to inconsistent results over time and from individual to individual.

SUMMARY OF THE INVENTION

The present invention solves the prior art problems discussed above and provides a distinct advance in the state of the art. In particular, the system enables the objective measurement of marbling in the muscular tissue of live cattle.

In the preferred embodiment, an ultrasound device is used to produce image data from the muscle tissue in live cattle wherein the image data is in the form of pixels having respective grey levels. The image data is then analyzed in a computer to produce a value or score representative of marbling. In preferred forms, the marbling score is determined as a function of pixel value correlation in a co-occurrence matrix, partial autocorrelation and nonspeckle area. Other preferred aspects of the present invention are set forth hereinbelow.

DETAILED DESCRIPTION OF THE PREFERRED EMBODIMENT

Figure 1:
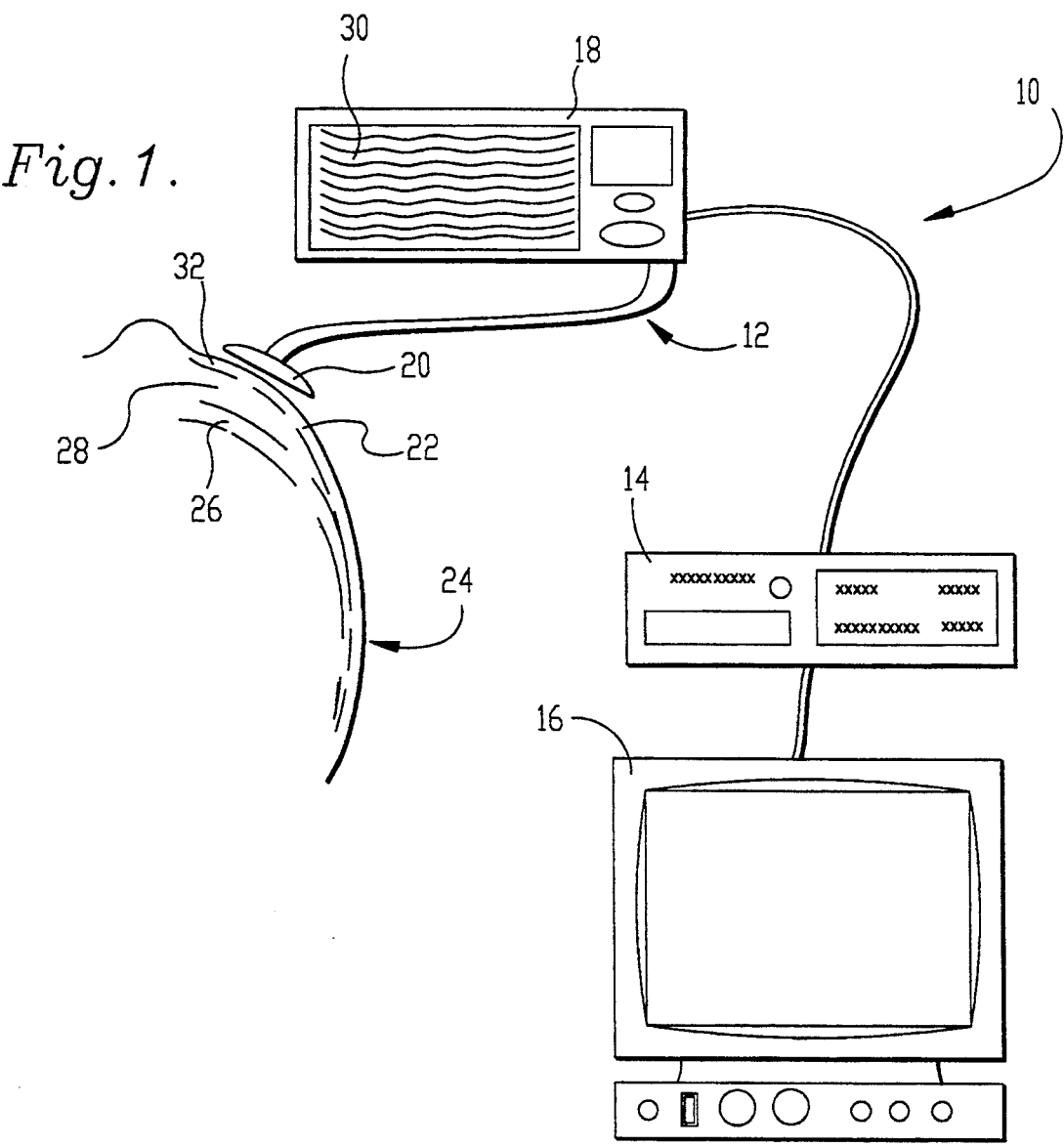
FIG. 1 illustrates the preferred apparatus in accordance with the present invention shown in use.

FIG. 1 illustrates preferred apparatus 10 including ultrasound device 12, video cassette recorder (VCR) 14 and computer 16. Device 12 is preferably Aloka model 210 distributed by Corometrics Medical Systems, Inc., of Wallingford, Conn. operable in real time in the so-called B-mode for producing a two dimensional echogram with pixel brightness indicating signal strength and having a refresh rate of 30 times per second. Images are stored in a four bit format providing 16 levels of grey scale. Device 12 includes signal processor 18 coupled with probe 20, which is preferably Aloka model UST-5021 that operates as a phased array probe with a 3.5 MHz central frequency and a 125 mm window.

VCR 14 is a conventional unit such as a Sharp VC-A5630 or preferably a Sony SLV-757VC coupled with signal processor 18 for receiving and recording about 30 seconds of real time imaging from ultrasound device 12. Computer 16 is preferably a Zenith A-386/25 personal computer equipped with Sony Trinitron monitor. Computer 16 includes a Targa M8 image capture board available from Truevision of Indianapolis, Ind., coupled with VCR 14 for receiving and digitizing images therefrom.

In use, probe 20 is placed on the surface 22 of live stock 24. More particularly, the insonation site is moistened with mineral oil as a couplant between probe 20 and surface 22 to minimize ultrasound attenuation. The preferred probe site is over the twelfth rib 26 beginning at the juncture of the rib and the spinous process at the vertebrae in order to develop a cross sectional image of the longissimus dorsi, i.e., ribeye, muscle 28 near the region where the carcass is to be cut into quarters. In this way, the image is of the same site presented to the grader for marbling classification. The gain of ultrasound device 12 is set at maximum in order to provide an image completely through longissimus muscle 28.

Probe 20 is manipulated laterally so that it follows the curvature of rib 26 until a full tomogram of muscle 28 comes into view on display 30 of signal processor 18, bracketed between backfat layer 32 and rib 26. In preferred practice, it is desired to record about 30 seconds of images from ultrasound device 12 to VCR 14.

Figure 2:
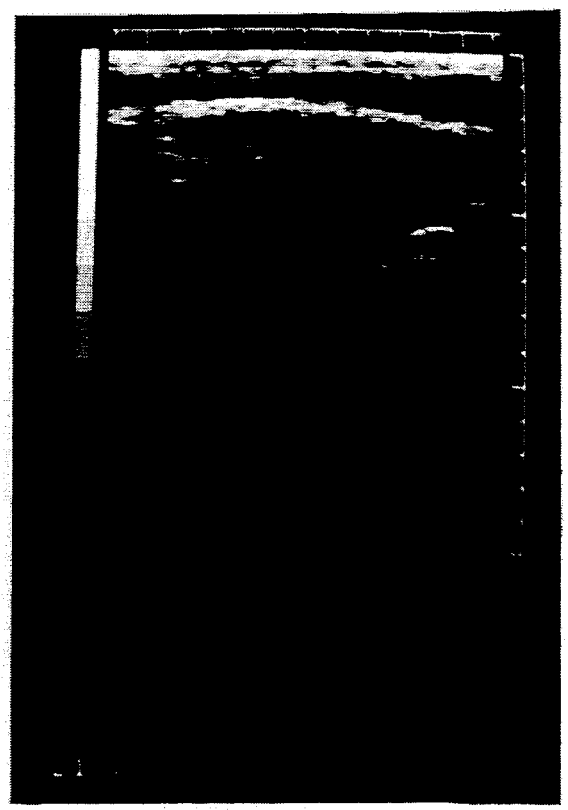
FIG. 2 is a photographic illustration of an ultra-sonic echogram correlated with a grade of USDA Low Select.
Figure 3:
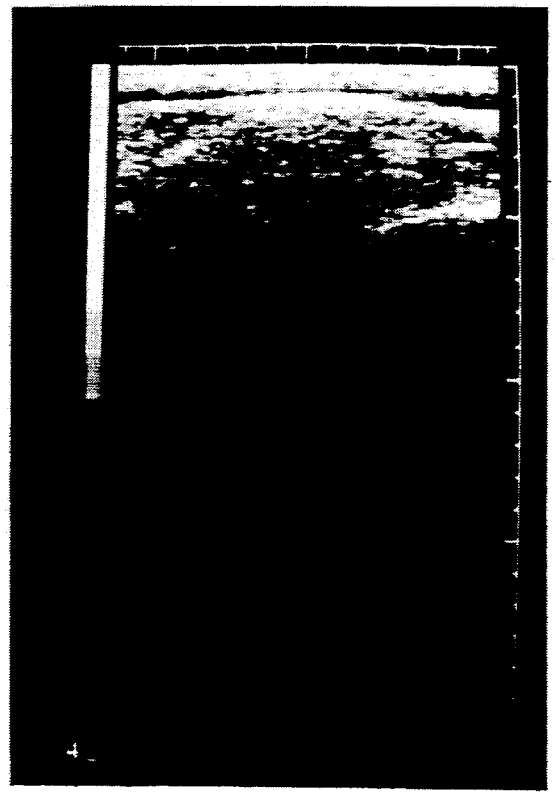
FIG. 3 is a photographic illustration of an ultra-sonic echogram correlated with a grade of USDA High Choice.

FIGS. 2 and 3 are photographic illustrations of ultrasonic images produced by device 12 as presented on display 30 and as recorded by VCR 14. As illustrated in these images, and with reference to FIG. 1, the upper layer depicts backfat layer 32 and the curved portion in the lower right of each image shows rib 26 with the area inbetween being muscle 28. As illustrated, the area of muscle 28 shows white patches known as speckle. Intramuscular fat in this area causes random scattering of the ultrasound waves and because of this, the marbling itself is not imaged. Instead, it is the scattering caused by the marbling that results in signal noise that is imaged as the white patches in the area of muscle 28 in FIGS. 2 and 3. A comparison of these two figures illustrates that the higher level of marbling in FIG. 3 produces the higher level of signal noise known as "speckle" in the region near backfat layer 32.

After the image recordation process is complete as described above, three to five representative frames are selected, digitized and stored in computer 16 as image data representative of the ultrasound image as pixels with eight bits defining 256 grey level values. Ultrasound device 12, however, only portrays 16 grey levels and the digitizer maps these values to eight bits. Computer 16 includes Java video analysis software available from Jandel Scientific of Cote Madera, Calif., which is used to manipulate the computer monitor cursor for outlining and defining a selected region of interest of about 3 to 4 cm square presenting a resolution of about 27 pixels per centimeter of tissue with about 8,000 to 10,000 pixels total in the region.

The region of interest is selected to be centered between backfat layer 32 and rib 26 within muscle 28, and to present a uniform pattern while avoiding acoustical shadows. The region of interest is located in the sector of the longissimus that is distal from the midline of the animal because that area is more likely to present a more consistent pattern of speckle and random specular echoes. The image data of the region of interest of each captured frame are processed for the statistical features which are then averaged for further analysis. The image data are initially stored as a TIF file and then converted to an ASCII format so that the data is amenable to image analysis. The pixel values in the stored array are initially preprocessed by using statistical regression to adjust for signal attenuation remaining after gain compensation adjustments of the ultrasound signal processor 12.

As those skilled in the art will appreciate, a vast array of mathematical techniques are available for analyzing images. In the development of the present invention, about 500 different techniques were investigated. For example, it was found that conventional first order statistics such as mean pixel values as well as the second, third and fourth moments of those values were insufficient. As a result, second order statistics are used to evaluate the relationships among the pixel grey level values of the region of interest, primarily involving co-occurrence and run-length matrices. None of the standard procedures were found to be adequate for measuring intramuscular fat.

Accordingly, three variables were developed for building a multiple regression model. These image texture variables include partial autocorrelation, correlation in a co-occurrence matrix and nonspeckle area. These were calculate along pixel vectors that were in the dimension axial to beam transmission. Appendix I incorporated as part of the disclosure hereof illustrates the preferred program written in Fortran for analyzing the image data in computer 16.

The partial autocorrelation variable is a time series analysis used to analyze the pixel grey level values along a row in the time domain. More particularly, the preferred partial autocorrelation is the regression of a pixel value with the pixel value two steps behind it, independent of the values of the intervening pixels. This is obtained from a formula involving two autocorrelations of a pixel with the pixel at lag 1 and lag 2. The specific formula is:

$$AR2.1 = (AR2 - AR1^2)/(1 - AR1^2)$$

where AR2.1 is the partial autocorrelation of the grey level value on the pixel at lag 2 independent of the pixel at lag 1, AR2 is the autocorrelation of lag 2 and lag 0, and AR1 is the autocorrelation of lag 1 and lag 0.

The data are normalized to a mean of 0 so that the autocorrelation values are the same as autoregressions. This was performed on values in an eight bit format and across all rows as if they were one continuous vector. The values are negative and usually in the range of $-0.65$ to $-0.75$ with the values nearest 0 associated with the higher level of marbling.

For the correlation variable, a co-occurrence matrix is built by mapping a pixel value (grey level) with that of a neighbor at a designated distance, that is, from row vectors across the data set and with eight bit formatting. The matrix is made symmetrical by placing values both above and below the diagonal. The correlation statistic is calculated from the regression of matrix values to the column (or row) values so that a high correlation indicates a predominance along the trace (diagonal) of the matrix and measures the similarity of a pixel value with its designated neighbor. A high co-occurrence correlation is associated with a high degree of marbling and relates to an image with uniform visual texture.

The nonspeckle area variable measures the lack of speckle in the image and is inversely related to marbling. This variable is developed from the run length grey level matrix by assessing the length of runs of the same grey level value along a row in the matrix. Initially the pixel grey level values are mapped to the four bit level because the eight bit resolution is too fine for meaningful run-length intonation. The abscissa values of the run length matrix are normalized so that the mean and standard deviation of the run length are the same as grey level value.

The nonspeckle area is calculated by summing the cell values in the matrix multiplied by the square of the normalized run length and dividing by the square of the corresponding grey level:

$$\text{Nonspeckle area} = (\text{Summation } P(i,j)/N \cdot J^2/I_2) - 1$$

where P(i,j) is the element in the matrix, N is the total number of runs (this normalizes the procedure so that it is independent of the size of the region of interest), J is the normalized run length that corresponds to the cell, and I is the corresponding grey level. The value of "1" is subtracted to increase the dynamic range. The nonspeckle area is inversely related to marbling because it measures the predominance of long, low grey levels, which characterizes an image with low speckle and thus, low marbling.

While each of the variables discussed above relates to marbling, each presents a different relationship between the pixel grey levels and marbling. In order to enhance the utility of the measurement, these variables are used in a multiple regression model to develop a marbling score. In the preferred embodiment, the marbling score (MS) is formulated as: MS=17.91342+2.890843 * Correlation−5643.7574 * Nonspeckle Area+13.58639 * Partial Autocorrelation. Those skilled in the art will appreciate that the coefficients of the marbling score formula can vary as the calibration set of data expands.

Figure 4A:
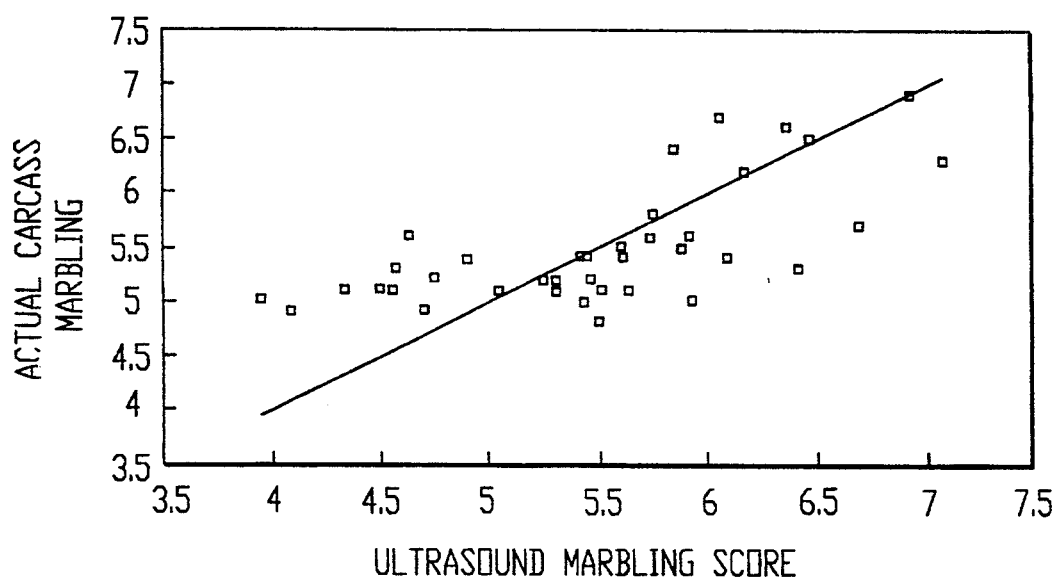
FIG. 4A is a graph representing a score of actual carcass marbling versus predicted carcass marbling using multiple regression analysis in accordance with the present invention.

FIG. 4A is a graph of actual carcass marbling scores as determined by inspection grading after slaughter versus marbling scores (MS) developed from the ultrasound image analysis discussed above. The straight line in the graph is the isopach line for perfect correspondence. As illustrated, the average deviation from isopach is 0.43.

Figure 4B:
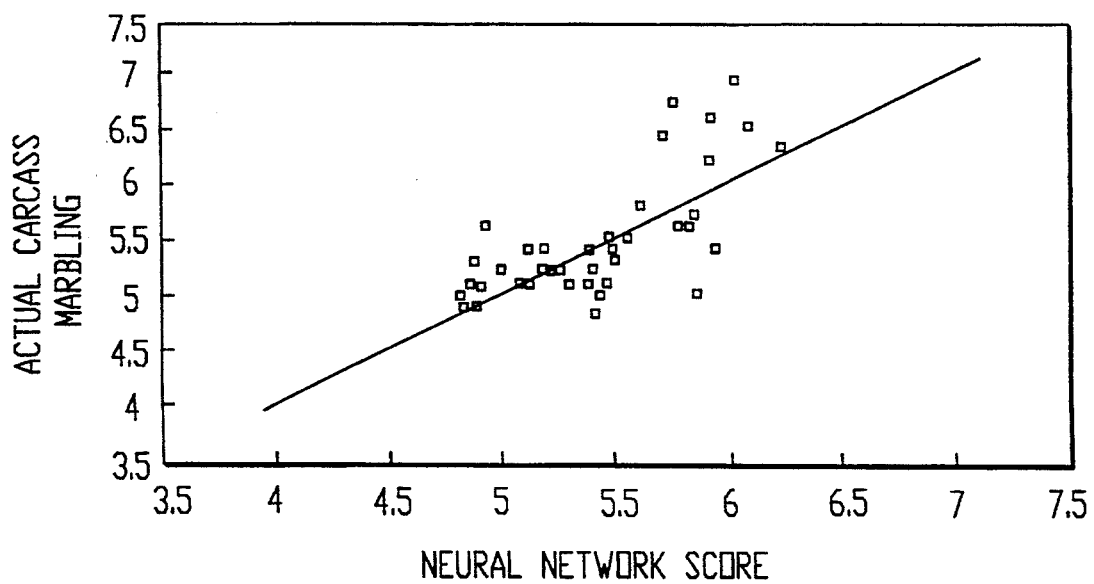
FIG. 4B is a graph representing scores of actual carcass marbling versus predicted marbling scores using neural network analysis in accordance with the present invention.

In another embodiment of the present invention, neural computing software such as Neuralworks Explorer by NeuralWare of Pittsburgh, Penn., was used to process the three marbling variables discussed above to develop a neural network score (NNS). This software was used in place of the marbling score (MS) formula. The results of this analysis are shown in FIG. 4B which is a graph of actual carcass marbling scores versus the neural network score. As illustrated, the average isopach deviation is 0.27.

As those skilled in the art will appreciate, the present invention encompasses many variations in the preferred embodiments described herein. For example, the output from ultrasound device 12 can be provided directly to computer 16 thereby eliminating the need for VCR 14. Additionally, each of the three marbling variables provide an independent measure of marbling from the ultrasound image and could be used singly or in combination with two in some circumstances. In addition, other techniques can be developed for developing marbling scores from the image texture variables.

Appendix I

```
C      PROGRAM REALTIME COMPLETED BY JRB MARCH 11, 1993
C      PARAMETIZATION OF ULTRASOUND IMAGE TO ESTIMATE MARBLING
C      INCLUDES OUTPUT FOR DIAGNOSTICS AND DEBUGGING
C      VARIABLES FOR INPUT AND FOR AUTOREGRESSION STATISTICS
       INTEGER*2 II,JJ,NROW,NCOL,LAG,LAG1,LAG2
       INTEGER*4 FILSIZ,SUM, X
       INTEGER*4 X1, X2, X3, Y1, Y2, X11, X22, X33, X12, X13,X1A,X11A
       INTEGER*2 PIXMAX, PIXMIN, FACTOR
       INTEGER*2 MATA (350,250)
       REAL*8 AVERAGE,SS1,SS1A,SS2,SS3,SS12,SS13,AR1,AR2,AR22,N,N1,REG
       REAL*8 S2,S3,K2,K3,SKEW
       REAL*8 STD, XMEAN
C
       CHARACTER*30 DIRECT
       CHARACTER*1  DELIM
       CHARACTER*8  CRDATE, FNAME
       CHARACTER*30 FILNAM,OUTFILE
       CHARACTER*12 FILNAME
       CHARACTER*22 MARBSCR, GRADE
C      VARIABLES FOR COOCCURRENCE MATRIX
       INTEGER*2 MAX1, MIN1, ELE, I, J, ELE1
       INTEGER*2 COOC (0:255,0:255)
       INTEGER*4 MATWK3 (0:255)
       INTEGER*4 MATWK4 (0:255)
       REAL*8 COR1 (256), COOR, NCOOR, HOMO
       REAL*8 COR2 (0:255)
       REAL*8 COR3 (0:255)
       REAL*8 MATWK5 (0:255), SUMB,SUMC
C      VARIABLES FOR RUN LENGTH AND SPECKLE ESTIMATOR
       REAL*8 SSUM, MARB
       INTEGER*2 MAX2, MIN2, MEAN,BIGC,ROW
       INTEGER*2 RUN (0:255,200)
       INTEGER*2 RUNC (200), RUNR (0:255)
       INTEGER*2 R1, LENGTH
       REAL*8 COLSUM, COLSQ, ROWSUM, ROWSQ, ROWMEAN, COLMEAN
       REAL*8 RUNJ (200)
       REAL*8 ROWSTD, COLSTD, SPECEST
C      **** END OF VARIABLE LIST ****
C
C      ENTER LOCATION OF TIFF DIRECTORY
10     FORMAT (' ENTER TIFF DIRECTORY  '\)
11     FORMAT (A6)
12     FORMAT (BN,I6)
       DIRECT = 'C:\JAVA\EXTRACT\TIFF.DIR'
       OUTFILE = 'C:\JAVA\EXTRACT\REG.WK3'
```

```
C      UNIT 1 IS THE TIFF.DIR FILE
       OPEN (UNIT=1, ACCESS='SEQUENTIAL',FILE= DIRECT, FORM=
      +'FORMATTED', MODE='READ', STATUS='OLD')
C      TIFF.DIR FILE HAS 5 EMPTY LINES
48     FORMAT (1X/1X/1X/1X/1X)
       READ (UNIT=1, FMT=48)
C      UNIT 5 IS THE DATA OUTPUT FILE
       OPEN (UNIT=5,ACCESS='SEQUENTIAL',FILE= OUTFILE,FORM='FORMATTED'
      +,MODE='WRITE',STATUS='UNKNOWN',BLOCKSIZE=2048)
49     FORMAT (A8,11A11)
       WRITE (5,49)'FILENAME','REGRESSION','MEAN','STD','SKEW','MEANRUN',
      +'OLDCORR','HOMO','AUTOREG', 'NEWCOOR', 'SPECEST',
      +'MARBSCORE'
C      *******************************
C      START LOOP
50     FORMAT (A8)
       READ (UNIT=1, FMT=50) FNAME
       LENGTH = LEN_TRIM(FNAME)
       FILNAM = 'C:\JAVA\EXTRACT\'//FNAME (:LENGTH) //'.'//'OUT'
51     FORMAT (A12)
C
C      THIS OPEN ALLOWS THE TIFF OUTPUT FILE TO BE WRITTEN TO DISK
C      UNIT 3 IS THE INDIVIDUAL OUTPUT FILE
C
       OPEN (UNIT=3,ACCESS='SEQUENTIAL',FILE= FILNAM,FORM='FORMATTED'
      +            ,MODE='READ', STATUS='UNKNOWN', BLOCKSIZE=8192)
C
C      * * * * * * * * * * * * * * * * * * * * * * * * * * *
C
       READ (3,57) FILNAME, FILSIZ, CRDATE,
      +            NCOL, NROW, PIXMIN, PIXMAX, X1, Y1, X2, Y2
57     FORMAT (1X, A12, 11X, I9, 16X, A8, 1X,
      +        4X, I4, 12X, I4, 21X,
      +        28X, I4, 4X,
      +        28X, I4, 2X,
      +        47X,
      +        5X,I5, 6X,I5, 11X, I5, 6X, I5)
C
58     FORMAT (1X, A12, ' containing', I9, ' bytes created  ', A8, 1X,
      +        ' has', I4, ' columns and  ', I4, ' rows of pixel data. ',
      +        ' The minimum pixel  value was', I4, ' and',
      +        ' the maximum pixel value was', I4, '. ',
      +        ' Area of interest is the rectangle bounded by: ',18X,
      +        ' X1 =',I5,' Y1 =',I5,' and  X2 =', I5, ' Y2 =', I5)
       WRITE (*,58) FILNAME, FILSIZ, CRDATE,
      +             NCOL, NROW, PIXMIN, PIXMAX, X1, Y1, X2, Y2
C
C      WRITE THE INDIVIDUAL PIXEL VALUES BY ROWS TO THE TIFF OUTPUT FILE
C
       WRITE (*,61)
59     FORMAT ('  FIRST AND LAST 3 PIXELS ARE',6(I3, 3X))
60     FORMAT (100(I3, A1))
61     FORMAT (' ')
       DO 62 II=1,NROW
          READ (3,60) (MATA(II,JJ), DELIM, JJ=1,NCOL)
62     CONTINUE
C
       WRITE(*,59) MATA(1,1), MATA(1,2), MATA(1,3), MATA(NROW,NCOL-2),
      +MATA(NROW,NCOL-1), MATA(NROW,NCOL)
       WRITE (*,61)
63     FORMAT ('  AUTOREGRESSION STATISTICS')
       WRITE (*,63)
C      ADJUST ROW VECTOR TO ZERO FOR AUTOREGRESSION ANALYSIS
C      AND ADJUST FOR INTERLACING FROM THE VCR TAPE
       DO 70 I=1, NCOL
70     MATWK3(I)=0
       X3=0
```

```
          SS2=0
          SS3=0
          X=0
         +'MARBSCORE'
C      *******************************************
C      START LOOP
50     FORMAT (A8)
       READ (UNIT=1, FMT=50) FNAME
       LENGTH = LEN_TRIM(FNAME)
       FILNAM = 'C:\JAVA\EXTRACT\'//FNAME (:LENGTH) //'.'//'OUT'
51     FORMAT (A12)
C
C      THIS OPEN ALLOWS THE TIFF OUTPUT FILE TO BE WRITTEN TO DISK
C      UNIT 3 IS THE INDIVIDUAL OUTPUT FILE
C
       OPEN (UNIT=3,ACCESS='SEQUENTIAL',FILE= FILNAM,FORM='FORMATTED'
      +          ,MODE='READ', STATUS='UNKNOWN', BLOCKSIZE=8192)
C
C      * * * * * * * * * * * * * * * * * * * * * * * * * * *
C
       READ (3,57) FILNAME, FILSIZ, CRDATE,
      +            NCOL, NROW, PIXMIN, PIXMAX, X1, Y1, X2, Y2
57     FORMAT (1X, A12, 11X, I9, 16X, A8, 1X,
      +        4X, I4, 12X, I4, 21X,
      +        28X, I4, 4X,
      +        28X, I4, 2X,
      +        47X,
      +        5X,I5, 6X,I5, 11X, I5, 6X, I5)
C
58     FORMAT (1X, A12, ' containing', I9, ' bytes created ', A8, 1X,
      +        ' has', I4, ' columns and ', I4, ' rows of pixel data. ',
      +        ' The minimum pixel value was', I4, ' and',
      +        ' the maximum pixel value was', I4, '. ',
      +        ' Area of interest is the rectangle bounded by: ',18X,
      +        ' X1 =',I5,' Y1 =',I5,' and X2 =', I5, ' Y2 =', I5)
       WRITE (*,58) FILNAME, FILSIZ, CRDATE,
      +             NCOL, NROW, PIXMIN, PIXMAX, X1, Y1, X2, Y2
C
C      WRITE THE INDIVIDUAL PIXEL VALUES BY ROWS TO THE TIFF OUTPUT FILE
C
       WRITE (*,61)
59     FORMAT (' FIRST AND LAST 3 PIXELS ARE',6(I3, 3X))
60     FORMAT (100(I3, A1))
61     FORMAT (' ')
       DO 62 II=1,NROW
           READ (3,60) (MATA(II,JJ), DELIM, JJ=1,NCOL)
62     CONTINUE
C
       WRITE(*,59) MATA(1,1), MATA(1,2), MATA(1,3), MATA(NROW,NCOL-2),
      +MATA(NROW,NCOL-1), MATA(NROW,NCOL)
       WRITE (*,61)
63     FORMAT (' AUTOREGRESSION STATISTICS')
       WRITE (*,63)
C      ADJUST ROW VECTOR TO ZERO FOR AUTOREGRESSION ANALYSIS
C        AND ADJUST FOR INTERLACING FROM THE VCR TAPE
       DO 70 I=1, NCOL
70     MATWK3(I)=0
       X3=0
       SS2=0
       SS3=0
       X=0
       SS1=NCOL-5
       DO 100 II=1, NROW
       SUM=0
       DO 90 JJ=6, NCOL
       SUM=SUM+MATA(II,JJ)
```

```
90      CONTINUE
        AVERAGE=SUM/SS1
        FACTOR=INT(AVERAGE+.5)
C       END ROW VECTOR ADJUSTMENT
C       DELETE FIRST 5 COLUMNS OF MATRIX (TO SQUARE IT)
        DO 95 JJ=6, NCOL
        ELE=MATA(II,JJ)
        X3=X3+ELE
        ELE=ELE-FACTOR
        ELE1=ELE+100
        X=X+ELE1
        SS1A=ELE1*ELE1
        SS2=SS2+SS1A
        SS3=SS3+SS1A*ELE1
        MATA(II,JJ-5)=ELE
        MATWK3(JJ-5)=MATWK3(JJ-5)+ELE
95      CONTINUE
100     CONTINUE
        CLOSE (UNIT=3, STATUS='KEEP')
        NCOL=NCOL-5
C       END COLUMN ADJUSTMENT
C       REGRESSION TO ADJUST FOR ATTENUATION
        X1=0
        X11=0
        X12=0
        X2=0
        DO 101 I=1,NCOL
        X1=X1+I
        X11=X11+I*I
        X12=X12+I*MATWK3(I)
101     X2=X2+MATWK3(I)
        SS1=NCOL
        REG=X1
        REG=(X12-X2*REG/SS1)/(X11-REG*REG/SS1)
        REG=REG/NROW
        SS1=NCOL*NROW
        XMEAN=X3/SS1
        SS1A=X
        STD=SS2-SS1A*SS1A/SS1
        S2=STD
        STD=SQRT(STD/(SS1-1))
C       CALCULATION OF SKEW
        S3=X
        S3=SS3-3*SS2*S3/SS1+2*S3*S3*S3/(SS1*SS1)
        K2=S2/(SS1-1)
        K3=SS1*S3/((SS1-1)*(SS1-2))
        SKEW = K3/SQRT(K2*K2*K2)
102     FORMAT (' REGRESSION ',F10.6,' MEAN ',F10.6,' STD ',F10.6,
       +' SKEW ',F10.6)
        WRITE (*,102) REG, XMEAN, STD, SKEW
        SS1=NCOL
        N=X1/SS1
        DO 103 J=1,NCOL
        SS3=REG*(J-N)
        IF (SS3.GE.0)II=SS3+.5
        IF (SS3.LT.0)II=SS3-.5
        DO 103 I=1,NROW
103     MATA(I,J)=MATA(I,J)-II
C       END REGRESSION ADJUSTMENT
C       ******  END ALL ARRAY ADJUSTMENTS ****
C       START AUTOCORRELATION ANALYSIS
        X1=0
        X1A=0
        X2=0
        X3=0
        X11=0
        X11A=0
```

```
            X12=0
            X13=0
            X22=0
            X33=0
            DO 110 II=1, NROW
            DO 105 JJ=2, NCOL
            LAG=MATA(II,JJ)
            LAG1=MATA(II,JJ-1)
            X1=X1+LAG
            X2=X2+LAG
            X11=X11+LAG*LAG
            X22=X22+LAG1*LAG1
            X12=X12+LAG*LAG1
            IF (JJ.GT.2) THEN
               LAG2=MATA(II,JJ-2)
               X1A=X1A+LAG
               X3=X3+LAG2
               X11A=X11A+LAG*LAG
               X33=X33+LAG2*LAG2
               X13=X13+LAG*LAG2
            END IF
105         CONTINUE
110         CONTINUE
            N=NROW*(NCOL-1)
            N1=NROW*(NCOL-2)
C           CONVERT FROM INTEGER TO REAL
            SS1=X1
            SS1=X11-SS1*SS1/N
            SS1A=X1A
            SS1A=X11A-SS1A*SS1A/N1
            SS2=X2
            SS2=X22-SS2*SS2/N
            SS3=X3
            SS3=X33-SS3*SS3/N1
            SS12=X2
            SS12=X12-X1*SS12/N
            SS13=X3
            SS13=X13-X1A*SS13/N1
            AR1=SS12/ SQRT(SS1*SS2)
            AR2=SS13/ SQRT(SS1A*SS3)
            AR22=(AR2-AR1*AR1)/(1-AR1*AR1)
C           AR22 IS THE PARTIAL CORRELATION COEFFICIENT OF LAG2 ON LAG0
C           INDEPENDENT OF LAG 1
113         FORMAT (10X,' AR1 = ',F10.6,'  AR2 = ',F10.6,'  AR22 = ',F10.6)
            WRITE (*,113) AR1,AR2,AR22
C           END AUTOCORRELATION ANALYSIS
C           ADJUST TO MEAN OF 100
            MAX1=0
            MIN1=256
            DO 115 II=1, NROW
            DO 114 JJ=1, NCOL
            ELE = MATA(II,JJ)+100
            MATA(II,JJ)=ELE
            IF (ELE.GT.MAX1) MAX1=ELE
            IF (ELE.LT.MIN1) MIN1=ELE
114         CONTINUE
115         CONTINUE
116         FORMAT(' MAX ADJUSTED VALUE = ',I3,'  MIN1 = ',I3)
118         FORMAT(I6)
            WRITE (*,116) MAX1, MIN1
C           END RECTIFYING TO MEAN OF 100
C           BUILD COOCCURRENCE MATRIX
            DO 119 II=0,255
            DO 119 JJ=0,255
119            COOC (II,JJ)=0
            DO 120 II=1, NROW
            DO 120 JJ=1, NCOL-12
```

```
            I=MATA(II,JJ)
            J=MATA(II,JJ+12)
            COOC(I,J)=COOC(I,J)+1
            COOC(J,I)=COOC(J,I)+1
120         CONTINUE
C     CALCULATE CORRELATION OF COOCCURRENCE MATRIX
C     OLD PROCEDURE FROM BASIC MATRIX MATH STATEMENTS
            DO 125 I=MIN1,MAX1
            MATWK3(I)=0
125         MATWK4(I)=0
            DO 130 I=MIN1, MAX1
            DO 130 J=MIN1, MAX1
            MATWK3(I)=MATWK3(I)+COOC(I,J)*J
            MATWK4(I)=MATWK4(I)+COOC(I,J)
130         CONTINUE
131         FORMAT (90I10)
            DO 150 I=MIN1, MAX1
            SS1=MATWK4(I)
            IF (MATWK4(I).GT.0) MATWK5(I)=MATWK3(I)/SS1
150         CONTINUE
            DO 155 I=MIN1,MAX1
155         COR2=0.0
            DO 160 I=MIN1, MAX1
            COR1(I)=I-MATWK5(I)
160         CONTINUE
            DO 170 I=MIN1, MAX1
            DO 170 J=MIN1, MAX1
            COR2(I)=COR2(I)+COOC(I,J)*COR1(J)
170         CONTINUE
            SUMB=0.0
            DO 175 I=MIN1, MAX1
            SUMB=SUMB+COR1(I)*COR2(I)
175         CONTINUE
            DO 180 I=MIN1, MAX1
            COR3(I)=COR1(I)*COR1(I)
180         CONTINUE
            DO 190 I=MIN1, MAX1
            DO 190 J=MIN1, MAX1
            COR2(I)=COR2(I)+COOC(I,J)*COR3(J)
190         CONTINUE
            SUMC=0.0
            DO 200 I=MIN1, MAX1
            SUMC=SUMC+COR2(I)
200         CONTINUE
            COOR=SUMB/SUMC
201         FORMAT (11X,' CORRELATION FROM COOCCURRENCE MATRIX =   ',
           +  F12.6)
            WRITE (*,61)
            WRITE (*,201) COOR
C     ALTERNATE COMPUTATION OF CORRELATION
C     (NEW AND MORE EFFICIENT FROM NICHOLAS)
            X11=0
            X12=0
            HOMO = 0.0
            DO 2002, I=MIN1,MAX1
2002        MATWK3(I)=0
            DO 202, I=MIN1, MAX1
            DO 202 J=MIN1,MAX1
            ELE=COOC(I,J)
            X12=X12+ELE*J*I
            MATWK3(I)=MATWK3(I)+ELE
            HOMO=HOMO+ELE*ELE
202         CONTINUE
            X11=NROW*(NCOL-12)*2
            SS1=0
            SS2=0
```

```
      DO 203 I=MIN1,MAX1
      SS1=SS1+MATWK3(I)*I*I
      SS2=MATWK3(I)*I+SS2
203   CONTINUE
      SS12=X12-SS2*SS2/X11
      SS13=SS1-SS2*SS2/X11
      NCOOR=SS12/SS13
      SS1=X11
      SS1=SS1*SS1
      HOMO=HOMO/SS1
206   FORMAT (' NEW CORR',F15.8,'      HOMO',F15.8)
C     NCOOR IS CORRELATION PARAMETER FROM COOCCURRENCE MATRIX
C     HOMO IS HOMOGENIETY PARAMETER
      WRITE (*,206)NCOOR,HOMO
C     BEGIN RUN LENGTH STATISTICS AND SPECKLE ESTIMATOR
C     RECTIFY TO 4 BIT ARRAY
      SUM = 0
      MIN2= 256
      MAX2= 0
      DO 210 I=1, NROW
      DO 210 J=1, NCOL
      ELE = MATA(I,J)/16
      MATA(I,J)=(ELE)
      SUM= SUM+ELE
      IF (ELE.LT.MIN2) MIN2=ELE
      IF (ELE.GT.MAX2) MAX2=ELE
210   CONTINUE
211   FORMAT (' MINIMUM BIT 4 VALUE ',I6,'     MAXIMUM VALUE  ',I6,)
      WRITE (*,211) MIN2, MAX2
      SSUM=SUM
      MEAN=INT(SSUM/(NROW*NCOL)+.5)
      MEAN = 100-MEAN
      MIN2=MIN2+MEAN
      MAX2=MAX2+MEAN
      DO 220 I=1, NROW
      DO 220 J=1, NCOL
      MATA(I,J)=MATA(I,J)+MEAN
220   CONTINUE
C     BUILD RUN-LENGTH MATRIX
      DO 222 I=1,256
      DO 222 J=1,200
222   RUN (I,J)=0
      BIGC=0
      DO 230 I=1,NROW
      R1=1
      DO 230 J=1,NCOL-1
      ROW=MATA(I,J)
      IF (ROW.EQ.MATA(I,J+1)) THEN
      R1=R1+1
      ELSE
      RUN(ROW,R1)=RUN(ROW,R1)+1
      IF (R1.GT.BIGC) BIGC=R1
      R1=1
      END IF
      IF (J.EQ.NCOL-1) THEN
      RUN(ROW,R1)=RUN(ROW,R1)+1
      IF (R1.GT.BIGC) BIGC=R1
      END IF
230   CONTINUE
231   FORMAT (' BIGGEST RUN =',I4)
      WRITE (*,231) BIGC
C     CALCULATE ROWSUM AND COLSUM MEAN AND STD
      SUM=0
      DO 232 I=MIN2,MAX2
232   RUNR(I)=0
      DO 234 J=1, BIGC
```

```
234     RUNC(J)=0
        DO 240 I=MIN2,MAX2
        DO 240 J=1, BIGC
        ELE=RUN(I,J)
        RUNR(I)=RUNR(I)+ELE
        RUNC(J)=RUNC(J)+ELE
        SUM=SUM+ELE
240     CONTINUE
        SSUM=SUM
        ROWSUM=0
        ROWSQ=0
        DO 250 I=MIN2, MAX2
        ROWSUM = ROWSUM + RUNR(I)*I
        ROWSQ = ROWSQ + RUNR(I)*I*I
250     CONTINUE
        COLSUM=0
        COLSQ=0
        DO 260 J=1, BIGC
        COLSUM = COLSUM + RUNC(J)*J
        COLSQ = COLSQ + RUNC(J)*J*J
260     CONTINUE
261     FORMAT (' SUM OF RUNS  ',I8,' MEAN RUN LENGTH ',F8.4)
        ROWMEAN = ROWSUM/SSUM
        COLMEAN = COLSUM/SSUM
        WRITE (*,261) SUM, COLMEAN
        ROWSTD = SQRT((ROWSQ-ROWSUM*ROWSUM/SSUM)/(SSUM-1))
        COLSTD = SQRT((COLSQ-COLSUM*COLSUM/SSUM)/(SSUM-1))
C       NORMALIZE RUN LENGTH VECTORS TO THE SAME MEAN AND STD OF
C       GRAY LEVEL VECTORS
        DO 270 J=1, BIGC
        RUNJ(J)=ROWMEAN-(ROWSTD/COLSTD)*(COLMEAN-J)
270     CONTINUE
        SPECEST = 0
        DO 280 I= MIN2, MAX2
        DO 280 J= 1, BIGC
        SPECEST = SPECEST + (RUN(I,J)/SSUM)*RUNJ(J)*RUNJ(J)/(I*I)
280     CONTINUE
        SPECEST = SPECEST - 1
281     FORMAT (40X,'  SPECEST = ',F12.8)
C       SPECEST IS THE FOURTH QUADRANT EMPHASIS IN THE RUN LENGTH
C       BY GRAY LEVEL MATRIX
        WRITE (*,281) SPECEST
C       REGRESSION MODEL FOR MARBLING SCORE
        MARB = 17.91342+2.890843*NCOOR-5643.7574*SPECEST+13.58639*AR22
282     FORMAT (20X,'  MARBLING SCORE = ',F12.4)
        WRITE (*,282) MARB
C       LOOKUP TABLE FOR CARCASS GRADE
        IF (MARB .LT.3.0) THEN
        MARBSCR = "PRACTICALLY DEVOID"
        GRADE = "LOW STANDARD"
        ELSE IF (MARB .LT. 4.0) THEN
        MARBSCR = "TRACES"
        GRADE = "STANDARD"
        ELSE IF (MARB .LT. 4.33) THEN
        GRADE = "LOW SELECT"
        MARBSCR = "SLIGHT AMOUNT MINUS"
        ELSE IF (MARB .LT. 4.67) THEN
        MARBSCR = "TYPICAL SLIGHT AMOUNT"
        GRADE = "AVERAGE SELECT"
        ELSE IF (MARB .LT. 5) THEN
        MARBSCR = "SLIGHT AMOUNT PLUS"
        GRADE = "HIGH SELECT"
        ELSE IF (MARB .LT. 6) THEN
        MARBSCR = "SMALL AMOUNT"
        GRADE = "LOW CHOICE"
        ELSE IF (MARB .LT. 7) THEN
        MARBSCR = "MODEST"
```

```
              GRADE = "AVERAGE CHOICE"
          ELSE IF (MARB .LT. 8) THEN
              MARBSCR = "MODERATE"
              GRADE = "HIGH CHOICE"
          ELSE IF (MARB .LT. 9) THEN
              MARBSCR = "SLIGHTLY ABUNDANT"
              GRADE = "LOW PRIME"
          ELSE IF (MARB .LT. 10) THEN
              MARBSCR = "MODERATELY ABUNDANT"
              GRADE = "AVERAGE PRIME"
          ELSE
              MARBSCR = "ABUNDANT"
              GRADE = "HIGH PRIME"
          END IF
290   FORMAT ('****MARBLING SCORE = ',A22,'  USDA GRADE = ',A22,)
      WRITE (*,61)
      WRITE (*,290) MARBSCR, GRADE
      WRITE (*,61)
295   FORMAT (A8,6(1X,F10.6),1X,F10.8,2(1X,F10.6),1X,F10.8,1X,F10.6)
C     AR22 NCOOR AND SPECEST ARE CRITICAL VARIABLES, HOWEVER, OTHERS
C     ARE SAVED FOR ONGOING TESTING (AND MAY BE OF VALUE AT SOME FUTURE
C     STAGE OF NEURAL NET ANALYSIS
C     SAVE FOR NEURAL NET LEARNING
      WRITE (5,295) FNAME, REG, XMEAN, STD, SKEW, COLMEAN, COOR, HOMO,
     +AR22,NCOOR, SPECEST, MARB
300   CONTINUE
      CLOSE (UNIT=1,STATUS='KEEP')
      CLOSE (UNIT=5, STATUS='KEEP')
      STOP 'Processing is complete'
      END
```

Having thus described the preferred embodiment of the present invention, the following is claimed as new and desired to be secured by Letters Patent:

1. A method of measuring intramuscular fat in an animal comprising the steps of:
providing an ultrasonic device operable for producing an ultrasound image from ultrasound waves, said device including a probe for transmitting and receiving ultrasound waves;
applying said probe to a selected surface portion of an animal for producing an ultrasound image of an interior muscle portion of the animal, the muscle portion including intramuscular fat, said ultrasound image including speckle produced by scattering of ultrasound waves by the intramuscular fat;
storing image data representative of said ultrasound image in a computer, said image data including data representative of said speckle and representing said ultrasound image as a plurality of pixels having respective grey levels; and
in said computer, analyzing said speckle in said image data for producing an output indicative of the intramuscular fat in the muscle portion, said analyzing step including the steps of calculating at least one of the variables included in the group comprising the partial autocorrelation of pixel grey levels with selected other pixel grey levels, the correlation of pixel grey levels in a co-occurrence matrix with the pixel values of selected neighbors in said matrix, and nonspeckle area indicated by a run length matrix of pixel grey levels and producing a marbling score without subjective judgment by an individual as a function of said at least one of the variables.

2. The method as set forth in claim 1, said analyzing step including the step of producing a marbling score as a function of all of said variables included in said group.

3. The method as set forth in claim 1, further including the step of determining said partial autocorrelation according to the formula $$AR2.1 = (AR2 - AR12)/(1 - AR12)$$

where AR2.1 is the partial autocorrelation of the grey level value on the pixel at lag 2 independent of the pixel at lag 1, AR2 is the correlation of lag 2 and lag 0, and AR1 is the correlation of lag 1 and lag 0 AR12 is the correlation of lag 1 and lag 2.

4. The method as set forth in claim 1, further including the step of determining said nonspeckle area according to the formula $$\text{nonspeckle area} = (\text{summation } P(i,j)/N*J^2/I) - 1$$

where P(i,j) is the element in the matrix, N is the total number of runs, J is the normalized run length that corresponds to the cell in the matrix, and I is the corresponding non-alleged grey level.

5. A apparatus for measuring intramuscular fat in an animal comprising:
an ultrasound device operable for producing an ultrasound image from ultrasound waves, said device including a probe for transmitting and receiving ultrasound waves; and
a computer including memory for storing image data representative of an ultrasound image received from said ultrasound device of an interior muscle portion of an animal produced by applying said probe to a selected surface portion of the animal, said ultrasound image including speckle produced by scattering of ultrasound waves by intramuscular fat within the muscle portion, said image data representing said ultrasound image as a pattern of pixels having respective grey levels;

said computer including analyzing means for analyzing said speckle in image data for producing an output indicative of the intramuscular fat in the muscle portion, said analyzing means including means for calculating at least one of the variables included in the group comprising the partial autocorrelation of pixel grey levels with selected other pixel grey levels, the correlation of pixel grey levels in a co-occurrence matrix with the pixel values of selected neighbors in said matrix, and nonspeckle area indicated by a run length matrix of pixel grey levels and means for producing a marbling score as a function of said at least one of the variables.

6. The apparatus as set forth in claim 5, said analyzing means including means for producing a marbling score as a function of all of said variables included in said group.

7. The apparatus as set forth in claim 5, wherein said partial autocorrelation is determined according to the formula $$AR2.1 = (AR2 - AR12)/(1 - AR12)$$

where AR2.1 is the partial autocorrelation of the grey level value on the pixel at lag 2 independent of the pixel at lag 1, AR2 is the autocorrelation of lag 2 and lag 0, and AR1 is the correlation of lag 1 and lag 0. AR12 is the correlation of lag 1 and lag 2.

8. The apparatus as set forth in claim 5, wherein said nonspeckle area is determined according to the formula $$\text{nonspeckle area} = (\text{summation } P(i,j)/N*J^2/I) - 1$$

where $P(i,j)$ is the element in the matrix, N is the total number of runs, J is the normalized run length that corresponds to the cell in the matrix, and I is the corresponding non-alleged grey level.

9. A method of measuring intramuscular fat in an animal comprising the steps of:
providing an ultrasonic device operable for producing an ultrasound image from ultrasound waves, said device including a probe for transmitting and receiving ultrasound waves;
applying said probe to a selected surface portion of an animal for producing an ultrasound image of an interior muscle portion of the animal, the muscle portion including intramuscular fat, said ultrasound image including speckle produced by scattering of ultrasound waves by the intramuscular fat;
storing image data representative of said ultrasound image in a computer, said image data including data representative of said speckle and representing said ultrasound image as a plurality of pixels having respective grey levels; and
in said computer, analyzing said speckle in said image data for producing an output indicative of the intramuscular fat in the muscle portion, said analyzing step including the steps of calculating the variables C as the correlation of pixel grey levels in a co-occurrence matrix with the pixel values of selected neighbors in said matrix, NA as the nonspeckle area indicated by a run length matrix of pixel grey levels, and PA as the partial autocorrelation of pixel grey levels with selected other pixel grey levels, and producing a marbling score as $$k_1 + k_2 C - k_3 NA + k_4 PA$$

where $k_1$, $k_2$, $k_3$ and $k_4$ are predetermined constants.

10. The method as set forth in claim 9, further including the step of determining said partial autocorrelation according to the formula $$AR2.1 = (AR2 - AR12)/(1 - AR12)$$

where AR2.1 is the partial autocorrelation of the grey level value on the pixel at lag 2 independent of the pixel at lag 1, AR2 is the autocorrelation of lag 2 and lag of and AR1 is the correlation of lag 1 and lag 0. AR12 is the correlation of lag 1 and lag 2.

11. The method as set forth in claim 9, further including the step of determining said nonspeckle area according to the formula $$\text{nonspeckle area} = (\text{summation } P(i,j)/N*J^2/I) - 1$$

where $P(i,j)$ is the element in the matrix, N is the total number of runs, J is the normalized run length that corresponds to the cell in the matrix, and I is the corresponding grey level.

* * * * *